United States Patent
Phelps (10) Patent No.: US 9,144,506 B2
(45) Date of Patent: Sep. 29, 2015

(54) INTERBODY AXIS CAGE

(76) Inventor: Jeff Phelps, North Richland Hills, TX (US)

(\*) Notice: Subject to any disclaimer, the term of this patent is extended or adjusted under 35 U.S.C. 154(b) by 386 days.

(21) Appl. No.: 13/564,813

(22) Filed: Aug. 2, 2012

(65) Prior Publication Data

US 2013/0041469 A1  Feb. 14, 2013

Related U.S. Application Data

(60) Provisional application No. 61/522,423, filed on Aug. 11, 2011.

(51) Int. Cl.
  *A61B 17/70* (2006.01)
  *A61F 2/44* (2006.01)
  *A61F 2/46* (2006.01)
  (Continued)

(52) U.S. Cl.
  CPC ............ *A61F 2/4455* (2013.01); *A61F 2/4611* (2013.01); *A61F 2/30965* (2013.01); *A61F 2002/2817* (2013.01); *A61F 2002/2835* (2013.01); *A61F 2002/30359* (2013.01); *A61F 2002/30433* (2013.01); *A61F 2002/30451* (2013.01); *A61F 2002/30635* (2013.01); *A61F 2002/30677* (2013.01); *A61F 2002/4415* (2013.01); *A61F 2002/4475* (2013.01); *A61F 2310/00017* (2013.01); *A61F 2310/00023* (2013.01); *A61F 2310/00029* (2013.01); *A61F 2310/00101* (2013.01); *A61F 2310/00161* (2013.01); *A61F 2310/00179* (2013.01);
  (Continued)

(58) Field of Classification Search
  CPC ............... A61B 17/64; A61B 17/6425; A61B 17/6433; A61B 17/70; A61B 17/7001; A61B 17/7002; A61B 17/7005; A61B 17/7007; A61B 17/7008; A61B 17/7011; A61B 17/7013; A61B 17/7014; A61B 17/7019; A61B 17/702; A61B 17/7022; A61B 17/7023; A61B 17/7025; A61B 17/7026; A61B 17/7029; A61B 17/7031; A61B 17/7032; A61B 17/7034; A61B 17/7035; A61B 17/7037; A61B 17/7038; A61B 17/7041; A61B 17/7049; A61B 17/705; A61B 17/7052
  USPC .................... 606/60, 246, 247, 250–279; 623/17.11–17.16
  See application file for complete search history.

(56) References Cited

U.S. PATENT DOCUMENTS 4,706,659 A \* 11/1987 Matthews et al. ............... 606/80
5,108,437 A \* 4/1992 Kenna ........................ 623/16.11
(Continued)

OTHER PUBLICATIONS

Sengupta, Dilip K., et al., "Biomechanical evaluation of immediate stability with rectangular verus cylindrical interbody cages in stabilization of the lumbar spine", BMC Musculoskeletal Disorders 2002, 3:23 11 pages.

*Primary Examiner* — Pedro Philogene
*Assistant Examiner* — Lynnsy Summitt
(74) *Attorney, Agent, or Firm* — Chainey P. Singleton; Daniel J. Chalker; Chalker Flores, LLP (57) ABSTRACT

An interbody axis cage for promoting stabilization and alignment of the spine following a surgical procedure is described herein. The interbody axis cage of the present invention has alternating points of axes in the X and Y direction that allow for 3-dimensional motion. The axis cage is roughly cylindrical in shape and it incorporates a threaded outerbody to facilitate screwing in and placement. The axis cage of the present invention is cannulated and incorporates a flexible reamer/cutter to "tap" for cage placement.

19 Claims, 2 Drawing Sheets

(51) Int. Cl.
  *A61F 2/30*     (2006.01)
  *A61F 2/28*     (2006.01)
(52) U.S. Cl.
  CPC ............... *A61F2310/00239* (2013.01); *A61F 2310/00407* (2013.01)

(56) References Cited

U.S. PATENT DOCUMENTS

| | | | |
|---|---|---|---|
| 5,554,194 A * | 9/1996 | Sanders | 623/17.17 |
| 5,556,431 A | 9/1996 | Buttner-Janz | |
| 5,649,925 A * | 7/1997 | Barbera Alacreu | 606/86 A |
| 5,879,352 A * | 3/1999 | Filoso et al. | 606/62 |
| 5,944,719 A * | 8/1999 | Leban | 606/59 |
| 6,001,130 A | 12/1999 | Bryan et al. | |
| 6,039,763 A | 3/2000 | Shelokov | |
| 6,224,600 B1 * | 5/2001 | Protogirou | 606/63 |
| 6,296,644 B1 * | 10/2001 | Saurat et al. | 606/256 |
| 6,387,130 B1 * | 5/2002 | Stone et al. | 623/17.16 |
| 6,572,619 B2 | 6/2003 | Santilli | |
| 6,770,096 B2 | 8/2004 | Bolger et al. | |
| 6,846,328 B2 | 1/2005 | Cauthen | |
| 7,344,564 B2 * | 3/2008 | Sweeney | 623/17.15 |
| 7,377,923 B2 | 5/2008 | Purcell et al. | |
| 7,563,281 B2 * | 7/2009 | Sears et al. | 623/17.11 |
| 7,621,912 B2 * | 11/2009 | Harms et al. | 606/59 |
| 7,682,400 B2 * | 3/2010 | Zwirkoski | 623/23.48 |
| 7,727,279 B2 * | 6/2010 | Zipnick et al. | 623/17.11 |
| 7,766,941 B2 * | 8/2010 | Paul | 606/257 |
| 7,785,325 B1 * | 8/2010 | Milbank | 606/62 |
| 7,806,913 B2 * | 10/2010 | Fanger et al. | 606/260 |
| 7,811,323 B2 | 10/2010 | Arnin et al. | |
| 7,824,445 B2 | 11/2010 | Biro et al. | |
| 7,828,825 B2 * | 11/2010 | Bruneau et al. | 606/260 |
| 7,857,854 B2 * | 12/2010 | Sweeney | 623/17.11 |
| 7,862,586 B2 * | 1/2011 | Malek | 606/246 |
| 7,875,059 B2 * | 1/2011 | Patterson et al. | 606/261 |
| 7,887,591 B2 | 2/2011 | Aebi et al. | |
| 7,909,875 B2 | 3/2011 | Zielinski et al. | |
| 7,909,878 B2 * | 3/2011 | Blatt et al. | 623/17.15 |
| 7,938,858 B2 * | 5/2011 | Miller et al. | 623/17.14 |
| 8,007,519 B2 * | 8/2011 | Hudgins et al. | 606/255 |
| 8,012,177 B2 * | 9/2011 | Jackson | 606/254 |
| 8,012,213 B2 * | 9/2011 | Sears et al. | 623/17.14 |
| 8,021,429 B2 * | 9/2011 | Viker | 623/17.16 |
| 8,025,681 B2 * | 9/2011 | Colleran et al. | 606/257 |
| 8,025,697 B2 * | 9/2011 | McClellan et al. | 623/17.11 |
| 8,029,548 B2 * | 10/2011 | Prevost et al. | 606/278 |
| 8,075,595 B2 * | 12/2011 | Kim | 606/257 |
| 8,114,133 B2 * | 2/2012 | Logan | 606/258 |
| 8,128,627 B2 * | 3/2012 | Justin et al. | 606/62 |
| 8,172,879 B2 * | 5/2012 | Butler et al. | 606/255 |
| 8,221,467 B2 * | 7/2012 | Butler et al. | 606/257 |
| 8,226,690 B2 * | 7/2012 | Altarac et al. | 606/256 |
| 8,241,362 B2 * | 8/2012 | Voorhies | 623/17.16 |
| 8,298,264 B2 * | 10/2012 | Betz et al. | 606/246 |
| 8,353,935 B2 * | 1/2013 | Krause | 606/256 |
| 8,372,074 B2 * | 2/2013 | Milbank | 606/59 |
| 8,382,757 B1 * | 2/2013 | Langmaid et al. | 606/59 |
| 8,388,658 B2 * | 3/2013 | Veldman et al. | 606/254 |
| 8,430,912 B2 * | 4/2013 | Veldman et al. | 606/257 |
| 8,449,574 B2 * | 5/2013 | Biedermann et al. | 606/246 |
| 8,486,112 B2 * | 7/2013 | Fanger et al. | 606/258 |
| 8,491,637 B2 * | 7/2013 | Matthis et al. | 606/254 |
| 8,506,599 B2 * | 8/2013 | Jackson | 606/264 |
| 8,512,407 B2 * | 8/2013 | Butler et al. | 623/17.16 |
| 8,535,351 B1 * | 9/2013 | Law | 606/257 |
| 8,568,452 B2 * | 10/2013 | Voorhies | 606/246 |
| 8,613,769 B2 * | 12/2013 | Sears et al. | 623/17.14 |
| 8,617,215 B2 * | 12/2013 | Marik et al. | 606/257 |
| 8,623,057 B2 * | 1/2014 | Jahng et al. | 606/255 |
| 8,623,059 B2 * | 1/2014 | Gerbec et al. | 606/256 |
| 8,685,022 B2 * | 4/2014 | Lorenz et al. | 606/59 |
| 8,690,922 B2 * | 4/2014 | Ritland | 606/255 |
| 8,690,923 B2 * | 4/2014 | Lynch | 606/260 |
| 8,702,758 B2 * | 4/2014 | Wang et al. | 606/257 |
| 8,721,690 B2 * | 5/2014 | Harms et al. | 606/254 |
| 2003/0187432 A1 * | 10/2003 | Johnson et al. | 606/59 |
| 2003/0187449 A1 * | 10/2003 | McCleary et al. | 606/80 |
| 2003/0220643 A1 * | 11/2003 | Ferree | 606/61 |
| 2004/0030388 A1 | 2/2004 | Null et al. | |
| 2005/0049943 A1 | 3/2005 | Alleyne et al. | |
| 2005/0065514 A1 * | 3/2005 | Studer | 606/61 |
| 2005/0071014 A1 * | 3/2005 | Barnett et al. | 623/19.14 |
| 2005/0125066 A1 * | 6/2005 | McAfee | 623/17.16 |
| 2005/0131407 A1 * | 6/2005 | Sicvol et al. | 606/61 |
| 2005/0154390 A1 * | 7/2005 | Biedermann et al. | 606/61 |
| 2005/0277922 A1 * | 12/2005 | Trieu et al. | 606/61 |
| 2005/0278023 A1 * | 12/2005 | Zwirkoski | 623/11.11 |
| 2006/0106381 A1 * | 5/2006 | Ferree et al. | 606/61 |
| 2006/0149242 A1 * | 7/2006 | Kraus et al. | 606/61 |
| 2006/0195093 A1 * | 8/2006 | Jahng | 606/61 |
| 2006/0229609 A1 * | 10/2006 | Wang | 606/61 |
| 2006/0264935 A1 * | 11/2006 | White | 606/61 |
| 2006/0264937 A1 * | 11/2006 | White | 606/61 |
| 2006/0287725 A1 | 12/2006 | Miller | |
| 2007/0049943 A1 | 3/2007 | Moskowitz et al. | |
| 2007/0093813 A1 * | 4/2007 | Callahan et al. | 606/61 |
| 2007/0093815 A1 * | 4/2007 | Callahan et al. | 606/61 |
| 2008/0051787 A1 * | 2/2008 | Remington et al. | 606/61 |
| 2008/0086135 A1 | 4/2008 | White | |
| 2008/0154306 A1 | 6/2008 | Heinz | |
| 2008/0161933 A1 | 7/2008 | Grotz et al. | |
| 2008/0262550 A1 | 10/2008 | Ferree | |
| 2008/0269753 A1 | 10/2008 | Cannestra | |
| 2009/0054991 A1 | 2/2009 | Biyani et al. | |
| 2009/0163953 A1 * | 6/2009 | Biedermann et al. | 606/254 |
| 2009/0182378 A1 * | 7/2009 | Choi | 606/254 |
| 2009/0192613 A1 | 7/2009 | Wing et al. | |
| 2009/0234388 A1 * | 9/2009 | Patterson et al. | 606/246 |
| 2009/0240285 A1 * | 9/2009 | Friedrich et al. | 606/255 |
| 2009/0259257 A1 * | 10/2009 | Prevost | 606/255 |
| 2009/0287250 A1 * | 11/2009 | Molz et al. | 606/247 |
| 2010/0057206 A1 | 3/2010 | Duffield et al. | |
| 2010/0160967 A1 * | 6/2010 | Capozzoli | 606/256 |
| 2010/0228295 A1 * | 9/2010 | Whitefield | 606/278 |
| 2011/0004249 A1 * | 1/2011 | Wu et al. | 606/254 |
| 2011/0029022 A1 * | 2/2011 | Zehnder et al. | 606/264 |
| 2011/0054616 A1 | 3/2011 | Kamran et al. | |
| 2011/0160774 A1 * | 6/2011 | Malek | 606/255 |
| 2012/0130432 A1 * | 5/2012 | Ferree et al. | 606/279 |
| 2012/0185048 A1 | 7/2012 | Phelps | |
| 2012/0209330 A1 * | 8/2012 | Jahng et al. | 606/254 |
| 2012/0310283 A1 * | 12/2012 | Morreale | 606/256 |
| 2013/0066375 A1 * | 3/2013 | Biedermann et al. | 606/260 |
| 2013/0090690 A1 * | 4/2013 | Walsh | 606/257 |
| 2013/0103091 A1 * | 4/2013 | Acosta et al. | 606/259 |
| 2013/0184755 A1 * | 7/2013 | Biedermann et al. | 606/255 |
| 2013/0226241 A1 * | 8/2013 | Thompson et al. | 606/254 |
| 2013/0226242 A1 * | 8/2013 | Trieu | 606/254 |
| 2013/0274803 A1 * | 10/2013 | Noordeen et al. | 606/256 |
| 2014/0018856 A1 * | 1/2014 | Matthis et al. | 606/255 |
| 2014/0088649 A1 * | 3/2014 | Refai | 606/256 |
| 2014/0180339 A1 * | 6/2014 | Ritland | 606/254 |

\* cited by examiner

INTERBODY AXIS CAGE

CROSS-REFERENCE TO RELATED APPLICATIONS

This application claims priority to U.S. Provisional Application Ser. No. 61/522,423, filed Aug. 11, 2011, the entire contents of which are incorporated herein by reference.

STATEMENT OF FEDERALLY FUNDED RESEARCH

None.

REFERENCE TO A SEQUENCE LISTING

None.

TECHNICAL FIELD OF THE INVENTION

The present invention relates in general to the field of spinal prosthesis, and more particularly, to an interbody axis cage and a method for sitting the same for providing improved spinal stability, alignment, and patient comfort following a spinal surgical procedure.

BACKGROUND OF THE INVENTION

Without limiting the scope of the invention, its background is described in connection with spinal joint prosthesis and methods and devices for enhancing spinal stability and alignment. A variety of artificial prosthesis are used to replace chronically injured or ruptured intervertebral discs and range from plate inserts, ball and socket joints, gel filled enclosures, spring-biased plates, plate and joint combinations and others.

For example, U.S. Patent Publication No. 20080262550 discloses methods for stabilizing upper and lower spinal vertebrae having a disc situated between the upper and lower vertebrae are described. First and second fasteners are inserted into the upper vertebra. Third and fourth fasteners are inserted into the lower vertebra. At least two of the first, second, third, and fourth fasteners are connected with an elongate element. In an alternative embodiment, at least three of the first, second, third, and fourth fasteners are connected with the elongate element. The elongate element may be an elastic connector or a cable. The elongate element may also have first and second ends that are connected by a crimp.

Another example is taught in U.S. Pat. No. 6,770,096 which relates to an interbody spinal stabilization method and an interbody spinal stabilization cage. The cage has a parallelepipedic shape and comprises a central hollow space intended to be filled with bone fragments. The cage also comprises anchoring device(s) having an overall S shape and opening onto lateral faces connecting with adjacent vertebrae, actuated by at least one actuation device opening into a front face. The anchoring device(s) each have at least one main cutting edge.

Another example of a spinal cage is taught in U.S. Patent Publication No. 20090054991, which discloses a spinal cage system for inserting a spinal cage assembly into a spine to separate and support adjacent spinal vertebrae, that includes a first cage member; a second cage member; and an articulating mechanism adapted to connect the first cage member to the second cage member and to permit the first and second cage members to move relate to each other. An insertion instrument is adapted to capture the spinal cage assembly for insertion of the spinal cage assembly into a spine and to rotate the first and second cage members relative to each other to achieve a desired orientation in the spine.

Finally, U.S. Pat. No. 7,824,445 discloses an improved artificial spinal implant system for replacing a disc or vertebral body that provides adjustability in height, and provides support and stability of the spine with proper lordosis or kyphosis, osseous-integration of the implant, and motion preservation (if desired) of the adjacent vertebrae while preserving the space. Motion preservation in the Biro invention is achieved with compressible and/or tiltable artificial discs.

BRIEF SUMMARY OF THE INVENTION

The present invention provides an interbody axis cage for promoting stabilization and alignment of the spine following a surgical procedure. The interbody axis cage of the present invention has alternating points of axes in the X and Y direction that allow for 3-dimensional motion and incorporates a threaded outerbody to facilitate screwing in and placement.

The present invention provides a flexible interbody axis cage for surgical implantation to support, stabilize, and/or align one or more vertebrae having a first segment having a first body segment that separates a first vertical tab at a distal segment end and a first horizontal slot at a proximal end positioned perpendicular to the first vertical tab, and a first tab pin aperture position in the first vertical tab, and a first slot pin aperture position in the first horizontal slot, wherein the first tab pin aperture is positioned perpendicular to the first slot pin aperture; a second segment having a second body segment that separates a second vertical tab at a distal segment end and a second horizontal slot at a proximal end positioned perpendicular to the second vertical tab, and a second tab pin aperture position in the second vertical tab, and a second slot pin aperture position in the second horizontal slot, wherein the second tab pin aperture is positioned perpendicular to the second slot pin aperture, wherein the second vertical tab mates to the first horizontal slot to align the first slot pin aperture and the second tab pin aperture to accept a first pivot pin; a third segment having a third body segment that separates a third vertical tab at a distal segment end and a third horizontal slot at a proximal end positioned perpendicular to the third vertical tab and a third tab pin aperture position in the third vertical tab, and a third slot pin aperture position in the third horizontal slot, wherein the third tab pin aperture is positioned perpendicular to the third slot pin aperture, wherein the third vertical tab mates to the second horizontal slot to align the second slot pin aperture and the third tab pin aperture to accept a second pivot pin; and wherein the first segment pivots about the first pivot pin and the third segment pivots about the second pivot pin relative to the second segment such that the first segment pivots in a direction perpendicular to the pivot direction of the third segment.

The present invention provides a flexible interbody axis cage adapted for surgical implantation to support, stabilize, align, or any combinations thereof one or more vertebrae having a disc space situated there between or a spinal column having a flexible frame, rod, or shaft for attachment or placement to a first side of the one or more vertebrae or the spinal column, wherein the frame, rod, or the shaft has a variable length central section extending between a distal end and a proximal end, wherein the central section comprises one or more cylindrical interlocking members or discs, wherein the flexible frame, rod, or shaft can be deformed to maintain a desired position; and one or more surgical or pedicle screws, fasteners, or any combinations thereof attached to the distal end, the proximal end, and at one or more points along a length of the flexible frame, rod, or the shaft, wherein the screws or the fasteners extend away from the frame, rod, or the shaft to aid in the attachment or the placement of the cage to the first side of the one or more vertebrae or the spinal column to support, stabilize, align, or any combinations thereof the one or more vertebrae or the spinal column.

The screws or the fasteners may be adapted to penetrate the disc space between the one or more vertebrae to attach the frame, the rod, or the shaft to the first side of the one or more vertebrae or the spinal column and the screws or the fasteners may be adapted to pass above and below the one or more vertebrae or the spinal column to encase the vertebrae or the spinal column.

The vertebrae or the spinal column may further include an additional axis cage attached or placed on a second side of the one or more vertebrae or the spinal column, wherein the axis cage having a flexible frame, rod, or shaft for attachment or placement to the second side of the one or more vertebrae or the spinal column, wherein the frame, rod, or the shaft has a variable length central section extending between a distal end and a proximal end, wherein the central section comprises one or more cylindrical interlocking members or discs, wherein the flexible frame, rod, or shaft can be deformed to maintain a desired position; and one or more surgical or pedicle screws, fasteners, or any combinations thereof attached to the distal end, the proximal end, and at one or more points along a length of the flexible frame, rod, or the shaft, wherein the screws or the fasteners extend away from the frame, rod, or the shaft to aid in the attachment or the placement of the cage to the second side of the one or more vertebrae or the spinal column to support, stabilize, align, or any combinations thereof the one or more vertebrae or the spinal column, wherein the screws or the fasteners may be adapted to penetrate the disc space between the one or more vertebrae or to pass above and below the one or more vertebrae or the spinal column to encase the vertebrae or the spinal column. The cage is capable of 3-dimensional motion and is roughly cylindrical in shape. The axis cage also includes a flexible reamer or a cutter to aid in cage placement. The rod or the shaft may be titanium, surgical alloys, stainless steel, chrome-molybdenum alloy, cobalt chromium alloy, zirconium oxide ceramic, non-absorbable polymers and other anticipated biocompatible metallic, ceramic or polymeric materials, and combinations thereof. The members or discs in the variable length central section comprises titanium, surgical alloys, stainless steel, chrome-molybdenum alloy, cobalt chromium alloy, zirconium oxide ceramic, non-absorbable polymers and other anticipated biocompatible metallic, ceramic or polymeric materials and combinations thereof.

The present invention provides a flexible interbody axis cage assembly adapted for surgical implantation to support, stabilize, align, or any combinations thereof one or more vertebrae having a disc space situated there between or a spinal column having a first flexible frame, rod, or shaft for attachment to a first side of the one or more vertebrae or the spinal column, wherein the frame, rod, or the shaft has a variable length central section extending between a distal end and a proximal end, wherein the central section comprises one or more cylindrical interlocking members or discs, wherein the first flexible frame, rod, or shaft can be deformed to maintain a desired position; a first set of one or more pedicle screws, fasteners, or any combinations thereof attached to the distal end, the proximal end, and at one or more points along a length of the first frame, rod, or shaft, wherein the screws or the fasteners extend away from the first frame, rod, or the shaft and are adapted to penetrate the disc space between the one or more vertebrae to attach the first frame, rod, or the shaft to the first side of the one or more vertebrae or the spinal column or to pass above and below the one or more vertebrae or the spinal column to encase the one or more vertebrae or spinal column; a second flexible frame, rod, or shaft for attachment to a second side of the one or more vertebrae or the spinal column, wherein the frame, rod, or the shaft has a variable length central section extending between a distal end and a proximal end, wherein the central section comprises one or more cylindrical interlocking members or discs, wherein the second flexible frame, rod, or shaft can be deformed to maintain a desired position; and a second set of one or more pedicle screws, fasteners, or any combinations thereof attached to the distal end, the proximal end, and at one or more points along a length of the second frame, rod, or shaft, wherein the screws or the fasteners extend away from the second frame, rod, or the shaft and are adapted to penetrate the disc space between the one or more vertebrae to attach the second frame, rod, or the shaft to the second side of the one or more vertebrae or the spinal column or to pass above and below the one or more vertebrae or the spinal column to encase the one or more vertebrae or spinal column, wherein the first and second set of screws and the fasteners may interlock in the disc space or above and below the one or more vertebrae or spinal column to support, stabilize, align, or any combinations thereof of the one or more vertebrae or the spinal column.

The present invention provides a device for stabilization, support, alignment, or any combinations thereof of one or more vertebrae or a spinal column following surgical or non-surgical treatment against one or more spinal disorders having an interbody axis cage assembly for surgical implantation or placement on or near the vertebrae or the spinal column, wherein the axis cage assembly comprises one or more units, wherein each unit with a flexible frame, rod, or shaft for attachment or placement to a side of the one or more vertebrae or the spinal column, wherein the frame, rod, or the shaft has a variable length central section extending between a distal end and a proximal end, wherein the central section comprises one or more cylindrical interlocking members or discs, wherein the flexible frame, rod, or shaft can be deformed to maintain a desired position; and a set of one or more surgical or pedicle screws, fasteners, or any combinations thereof attached to the distal end, the proximal end, and at one or more points along a length of the flexible frame, rod, or the shaft, wherein the screws or the fasteners extend away from the one or more frame, rod, or the shaft, wherein the screws or the fasteners are adapted to penetrate a disc space between the one or more vertebrae to attach the frame, rod, or the shaft to the side of the one or more vertebrae or the spinal column or to pass above and below the one or more vertebrae or the spinal column to encase the one or more vertebrae or spinal column to support, stabilize, align, or any combinations thereof the one or more vertebrae or the spinal column.

The present invention also provides a method for stabilization, alignment, support or any combinations thereof of one or more vertebrae or a spinal column following surgical or non-surgical treatment of one or more spinal conditions by identifying a subject in need of spinal stabilization, alignment, support or any combinations thereof following surgical or non-surgical treatment for one or more spinal conditions; and placing or implanting surgically an interbody axis cage assembly on or near the vertebrae or the spinal column of the subject, wherein the axis cage assembly comprises one or more units, wherein each unit having a flexible frame, rod, or shaft for attachment or placement to a side of the one or more vertebrae or the spinal column, wherein the frame, rod, or the shaft has a variable length central section extending between a distal end and a proximal end, wherein the central section comprises one or more cylindrical interlocking members or discs, wherein the flexible frame, rod, or shaft can be deformed to maintain a desired position; and a set of one or more surgical or pedicle screws, fasteners, or any combinations thereof attached to the distal end, the proximal end, and at one or more points along a length of the one or more flexible frame, rod, or the shaft, wherein the screws or the fasteners extend away from the frame, rod, or the shaft, wherein the screws or the fasteners are adapted to penetrate a disc space between the one or more vertebrae to attach the frame, rod, or the shaft to the side of the one or more vertebrae or the spinal column or to pass above and below the one or more vertebrae or the spinal column to encase the one or more vertebrae or spinal column to support, stabilize, align, or any combinations thereof the one or more vertebrae or the spinal column.

The present invention provides a method for protecting one or more vertebrae or a spinal column from injury following surgical or non-surgical treatment of one or more spinal conditions by identifying a subject in need of protection of one or more vertebrae or the spinal column following surgical or non-surgical treatment for one or more spinal conditions; and placing or implanting surgically an interbody axis cage assembly on or near the vertebrae or the spinal column of the subject to encase the one or more vertebrae or the spinal column, wherein the axis cage assembly comprises one or more units, wherein each unit with a flexible frame, rod, or shaft for attachment or placement to a side of the one or more vertebrae or the spinal column, wherein the frame, rod, or the shaft has a variable length central section extending between a distal end and a proximal end, wherein the central section comprises one or more cylindrical interlocking members or discs, wherein the flexible frame, rod, or shaft can be deformed to maintain a desired position; and a set of one or more surgical or pedicle screws, fasteners, or any combinations thereof attached to the distal end, the proximal end, and at one or more points along a length of the one or more flexible frame, rod, or the shaft, wherein the screws or the fasteners extend away from the frame, rod, or the shaft, wherein the screws or the fasteners are adapted to pass above and below the one or more vertebrae or the spinal column to encase the one or more vertebrae or spinal column to protect the one or more vertebrae or the spinal column.

BRIEF DESCRIPTION OF THE SEVERAL VIEWS OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention describes an interbody axis cage with alternating points of axes in the X and Y direction that allow for 3-dimensional motion. The axis cage of the present invention is roughly cylindrical in shape and it incorporates a threaded outerbody to facilitate screwing in. The axis cage of the present invention is cannulated and incorporates a flexible reamer/cutter to "tap" for cage placement.

The spine encloses the spinal cord and includes thirty-three vertebrae. The vertebrae are divided into four regions that include the uppermost seven vertebrae referred to as the cervical vertebrae, followed sequentially by the twelve thoracic vertebrae, the five lumbar vertebrae and the five sacral vertebrae. The final four vertebrae are referred to as the coccygeal vertebrae.

Although the vertebrae of each region have a different structure, the basic vertebra structure has certain similarities. The vertebral body is the anterior part of the vertebra and is roughly cylindrical. The vertebral body has a superior surface that is concave transversely and convex antero-posterioly with prominent elevations on each side. Two articular facets on the inferior surface of the body articulate with the uncinate processes. Additionally, the posterior arch is formed by the pedicles, the articular processes, the laminae and the spinous processes. The vertebral pedicles are short and thick regions projecting backwards and slightly laterally from the vertebral body. The articular processes are located at the junction of the pedicles and laminae and are made up of the superior articular process that articulates with the above vertebra and the inferior articular process that articulates with the vertebra below it. The laminae are long and thin, extending backwards and medially from the pedicle to meet the midline thereby completing the posterior arch. The spinous processes project backwards from the junction of the laminae. Transverse processes arise anteriorly from the vertebral body and posteriorly from the articular processes to form the vertebral foramen. The vertebral foramen is the triangular region occupied by the spinal cord, meninges and associated vessels. Additionally, the vertebrae cephalad to the sacral vertebrae are united by articular capsules and by ligaments and separated by fibrocartilaginous intervertebral discs. The outside surface of the vertebral body is made of a relatively strong cortical bone layer, while the center of the vertebral body is made of a weak cancellous bone.

The vertebral bodies are separated by intervertebral discs, which provide the majority of the weight bearing support of the vertebral column. The intervertebral discs include a cartilage shell enclosing a central mass that provides cushioning and dampening of compressive forces applied to the vertebral bodies and the spinal column. Generally, the central mass is relatively inelastic, but can bulge outward to accommodate loads applied axially to the spinal.

The successive positioning of the vertebral body allows the vertebral foramen to surround the spinal cord and retain articulation of the vertebrae and extend posteriorly of the spinal canal. The complicated vertebral structure, the degree of spinal articulation and complicated network of connective elements make the spine susceptible to many forms of damage, e.g., traumatic spinal injuries, tumors, infections, surgeries, disease processes, aging processes, and congenital abnormalities. Various types of spinal column disorders are known and include degenerative disc disease, excess lordosis (abnormal backward curvature of the spine), fractured vertebra, kyphosis (abnormal forward curvature of the spine), ruptured discs, scoliosis (abnormal lateral curvature of the spine), slipped discs, spondylolisthesis (abnormal forward displacement of vertebra) and the like.

The figures depict specific embodiments of the present invention used for support and alignment of the spine. As will be disclosed in detail herein, the present invention will have wide applicability to a number of different locations and for replacement of many different types of joints. The axis cage depicted in the figures, are non-limiting examples of the present invention. In addition the present invention includes embodiments that are used in other locations in the body and various cages. The variable angle attachment mechanism of the present invention may be used in various medical devices known to the skilled artisan.

Figure 1:
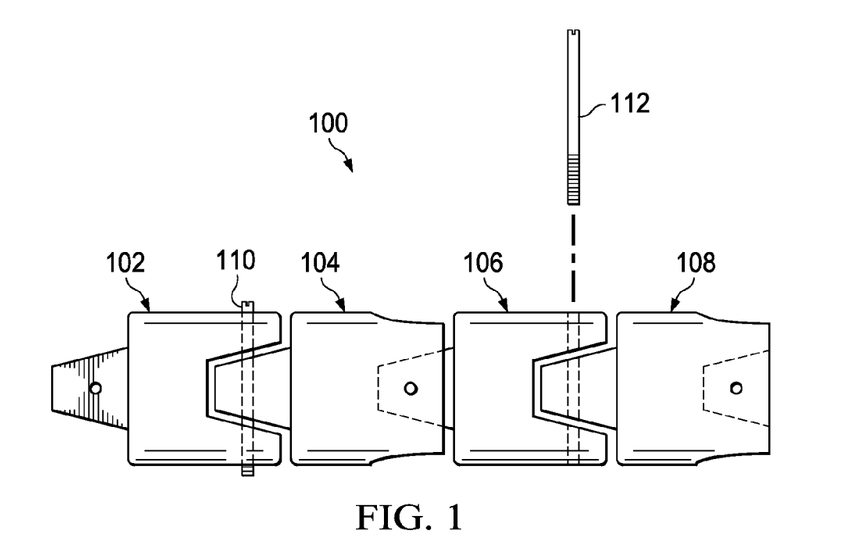
FIG. 1 is a front view of the interbody axis cage of the present invention.

FIG. 1 is a front view of an interbody axis cage 100 of the present invention. Cage 100 comprises a plurality of interconnected discs 102, 104, 106, and 108. The discs are interconnected by placing or insertion through an aperture (not shown) and once inserted through the aperture the inserted discs are held in place by screws/fasteners (110 and 112).

Figure 2A:
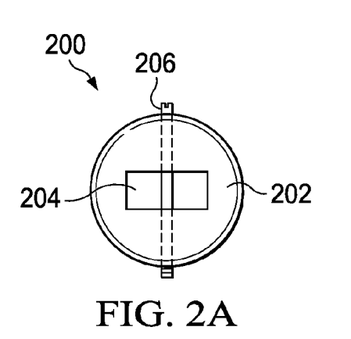
FIGS. 2A-2C are end views of the interbody axis cage of the present invention showing the aperture for receiving the disc and the fasteners for attachment to the spine.

FIG. 2A is an end view of the interbody axis cage showing a disc 200, with an aperture 204 (for insertion of a subsequent disc). The disc surface is shown in 202, and a screw/fastener holding the disc in place in the aperture 204 is shown in 206.

Figure 2B:
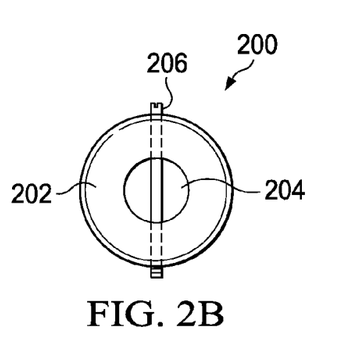

FIG. 2B is an end view of the interbody axis cage showing a disc 200, with an aperture 204 (for insertion of a subsequent disc). The disc surface is shown in 202, and a screw/fastener holding the disc in place in the aperture 204 is shown in 206. The aperture 204 is depicted as an oval or a circle in this embodiment but may be any shape depending on the application.

Figure 2C:
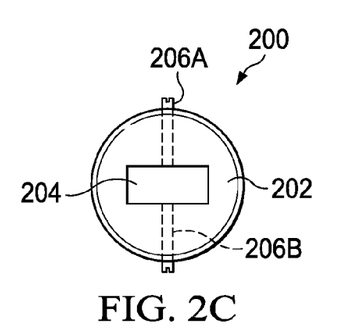

FIG. 2C is an end view of the interbody axis cage showing a disc 200, with an aperture 204 (for insertion of a subsequent disc). The disc surface is shown in 202, and a screw/fastener holding the disc in place in the aperture 204 is shown in 206A-206B. The screw/fastener 206A-206B may be position in the side of the device as to not penetrate the aperture 204 allowing the aperture 204 to be unobstructed. The screw/fastener 206A-206B may be inserted into the side and terminated prior to the aperture 204. In addition it is possible to have a combination of different types of screw/fasteners in a single device. For example, the device may include a screw/fastener 206A-206B be position in the side of the device to penetrate the aperture 204 allowing the aperture 204 to be partially obstructed. The next segment includes a screw/fastener 206A-206B be inserted into the side and terminated prior to the aperture 204 allowing the aperture 204 to be partially unobstructed. This can be repeated or varied as necessary for the insertion.

Figure 3:
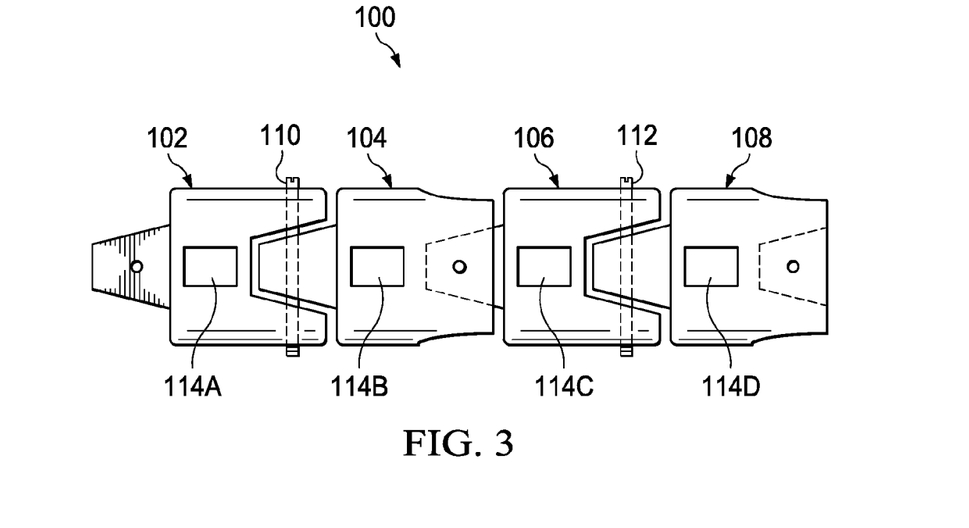
FIG. 3 is a front view of another embodiment of the interbody axis cage of the present invention.

FIG. 3 is a front view of an interbody axis cage 100 of the present invention. Cage 100 comprises a plurality of interconnected discs 102, 104, 106, and 108. The discs are interconnected by placing or insertion through an aperture (not shown) and once inserted through the aperture the inserted discs are held in place by screws/fasteners (110 and 112). The inter-connected discs 102-108 each have a window 114A-114D that is depicted here as rectangular but may be of any shape and/or any size or depth. The window 114A-114D may contain one or more active agents known to the skilled artisan, e.g., antibiotics, active agents, growth agents, and so forth. The windows 114A-114D is to allow for the placement and housing for one or more grafts materials. The windows 114A-114D may individually have graft materials, active agents or a combination thereof.

Figure 4A:
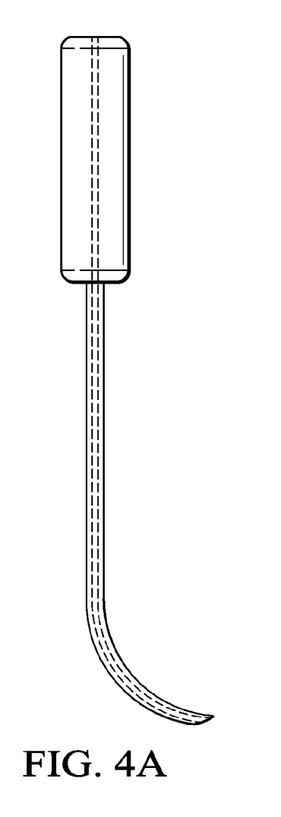
FIGS. 4A and 4B are images of cannulated insertion device and a cannulated reamer respectively.
Figure 4B:
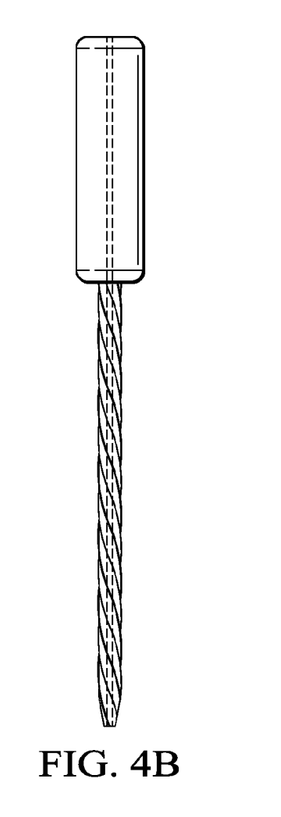

FIGS. 4A and 4B are images of cannulated insertion device and a cannulated reamer, respectively. The cannulated insertion device depicted in FIG. 4A allows the insertion in difficult to access regions without additional incisions for access. The cannulated insertion device allows the passage of a wire or other material through the device and change the angle of exit from the cannulated insertion device. Therefore allowing access to more limited regions. FIG. 4B depicted a cannulated reamer. The cannulated insertion device and a cannulated reamer allow a less invasive method of insertion. The flexible reamer or a cutter may be used to aid in cage placement.

The discs of the present invention may be fabricated from generally biocompatible materials including, without limitation, titanium, surgical alloys, stainless steel, chrome-molybdenum alloy, cobalt chromium alloy, zirconium oxide ceramic, non-absorbable polymers and other anticipated biocompatible metallic, ceramic or polymeric materials and combinations thereof. The discs may be fabricated from different materials and may even be fabricated by using different materials within each disc. Certain materials may even be used to coat a portion or all of a disc, e.g., a titanium disc may be fused, welded, melted, coated, impregnated or infused along it's a portion or all of its periphery with a ceramic or a polymer. Alternatively, the fused, welded, melted, coated, impregnated or infused material may be on a portion or all of one surface but not another, or may completely surround the disc.

The components of the present invention may be constructed from any suitable similar or dissimilar materials (e.g., titanium, a titanium alloy, a metal, an alloy, a stainless steel, a composite, a polymer, a blend of polymers, a carbon fiber, a plastic, a thermoplastic, a ceramic, carbon nanotubes, a synthetic material or other material known to the skilled artisan) depending on the particular need or application. In addition, combinations and mixtures of material may be used, e.g., ceramic coated metal, carbon nanotube coated metal and/or ceramic, polymer coated metal and/or ceramic, a magnetic material combined with a polymer, an electrical conductive material combined with a polymer, metal, plastic, etc. and so-forth. For example, polymers and many lightweight and remarkably strong materials that include a reinforced two-phase material, carbon fiber reinforced plastic, carbon fiber, plastic, polymers or combinations thereof. Polymers such as silicone, polyethylene, nylon, vinyl, methylmethacyrate, dacrons or teflon may be used. The screws may be made of a strong material (e.g., metal, magnamite graphite fiber, carbon reinforced plastic) so as to prevent the screws from being sheared off by the stress of the system. Additionally, porous material in which the porosity is controlled by the replamine form process may be used. The materials used are not limited to the above noted and may also include other suitable solid materials that have the above-noted properties.

The present invention provides a method of inserting the instant device that includes placing a curved guidewire guide about the disc space. A guidewire is then placed into position across the disk space. A reamer is then passed over the guidewire and material removed. This process is repeated with increasingly larger reamers to remove the disk material and perform endplate preparations. A treaded flexible implant (of the correct diameter) is then threaded into position.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A flexible interbody axis cage for surgical implantation to support, stabilize, and/or align one or more vertebrae comprising:
   a first segment having a first body segment that separates a first vertical tab at a distal segment end and a first horizontal slot at a proximal end positioned perpendicular to the first vertical tab, and a first tab pin aperture positioned in the first vertical tab, and a first slot pin aperture positioned in the first horizontal slot, wherein the first tab pin aperture is positioned perpendicular to the first slot pin aperture;
   a second segment having a second body segment that separates a second vertical tab at a distal segment end and a second horizontal slot at a proximal end positioned perpendicular to the second vertical tab, and a second tab pin aperture positioned in the second vertical tab, and a second slot pin aperture positioned in the second horizontal slot, wherein the second tab pin aperture is positioned perpendicular to the second slot pin aperture, wherein the second vertical tab mates to the first horizontal slot to align the first slot pin aperture and the second tab pin aperture to accept a first pivot pin;
   a third segment having a third body segment that separates a third vertical tab at a distal segment end and a third horizontal slot at a proximal end positioned perpendicular to the third vertical tab and a third tab pin aperture positioned in the third vertical tab, and a third slot pin aperture positioned in the third horizontal slot, wherein the third tab pin aperture is positioned perpendicular to the third slot pin aperture, wherein the third vertical tab mates to the second horizontal slot to align the second slot pin aperture and the third tab pin aperture to accept a second pivot pin; and
   wherein the first segment pivots about the first pivot pin and the third segment pivots about the second pivot pin relative to the second segment such that the first segment pivots in a direction perpendicular to the pivot direction of the third segment.

2. The flexible interbody axis cage of claim 1, wherein the first pivot pin and the second pivot pin comprise threads that mate to screw fittings in the respective slot pin apertures to secure the pivot pins.

3. The flexible interbody axis cage of claim 1, further comprising at least one additional segment each having a body segment that separates a vertical tab at a distal segment end and a horizontal slot at a proximal end positioned perpendicular to the vertical tab, and a tab pin aperture positioned in the vertical tab, and a slot pin aperture positioned in the horizontal slot, wherein each vertical tab mates to the horizontal slot of the adjacent segment to increase the length of the flexible interbody axis cage.

4. The flexible interbody axis cage of claim 1, wherein the flexible interbody axis cage comprises titanium, surgical alloys, stainless steel, chrome-molybdenum alloy, cobalt chromium alloy, zirconium oxide ceramic, non-absorbable polymers and other anticipated biocompatible metallic, ceramic or polymeric materials, and combinations thereof.

5. A flexible interbody axis cage adapted for surgical implantation to support, stabilize, and/or align one or more vertebrae comprising:
   a flexible frame for placement about a first side of one or more vertebrae, wherein the flexible frame has a variable length central section extending between a distal end and a proximal end, wherein the central section comprises a first segment having a first body segment that separates a first vertical tab at a distal segment end and a first horizontal slot at a proximal end positioned perpendicular to the first vertical tab, and a first tab pin aperture positioned in the first vertical tab, and a first slot pin aperture positioned in the first horizontal slot, wherein the first tab pin aperture is positioned perpendicular to the first slot pin aperture; a second segment having a second body segment that separates a second vertical tab at a distal segment end and a second horizontal slot at a proximal end positioned perpendicular to the second vertical tab, and a second tab pin aperture positioned in the second vertical tab, and a second slot pin aperture positioned in the second horizontal slot, wherein the second tab pin aperture is positioned perpendicular to the second slot pin aperture, wherein the second vertical tab mates to the first horizontal slot to align the first slot pin aperture and the second tab pin aperture to accept a first pivot pin; a third segment having a third body segment that separates a third vertical tab at a distal segment end and a third horizontal slot at a proximal end positioned perpendicular to the third vertical tab and a third tab pin aperture positioned in the third vertical tab, and a third slot pin aperture positioned in the third horizontal slot, wherein the third tab pin aperture is positioned perpendicular to the third slot pin aperture, wherein the third vertical tab mates to the second horizontal slot to align the second slot pin aperture and the third tab pin aperture to accept a second pivot pin; and wherein the first segment pivots about the first pivot pin and the third segment pivots about the second pivot pin relative to the second segment such that the first segment pivots in a direction perpendicular to the pivot direction of the third segment; and one or more surgical fasteners adapted to attach to the distal end, the proximal end, and at one or more points along a length of the flexible frame to attach the flexible interbody axis cage to a first side of the one or more vertebrae to support, stabilize, and/or align the one or more vertebrae.

6. The axis cage of claim 5, wherein the surgical fasteners are adapted to penetrate a disc space between the one or more vertebrae to attach the flexible frame to the first side of the one or more vertebrae.

7. The axis cage of claim 5, wherein the surgical fasteners are adapted to pass above and below the one or more vertebrae or the spinal column to encase the vertebrae or the spinal column.

8. The axis cage of claim 5, further comprising a second interbody axis cage assembly comprising:
a flexible frame, rod, or shaft for attachment to a second side of the one or more vertebrae, wherein the flexible frame, rod, or the shaft has a variable length central section extending between a distal end and a proximal end, wherein the central section comprises one or more cylindrical interlocking members or discs, wherein the flexible frame, rod, or shaft can be deformed to maintain a desired position; and
one or more surgical or pedicle screws, fasteners, or any combinations thereof attached to the distal end, the proximal end, and at one or more points along a length of the flexible frame, rod, or the shaft, to attach the second interbody axis cage to a second side of the one or more vertebrae or the spinal column, wherein the screws or the fasteners may be adapted to penetrate a disc space between the one or more vertebrae or to pass above and below the one or more vertebrae or the spinal column to encase the vertebrae or the spinal column, wherein the interbody axis cage assembly has alternating axis in a X-plane and a Y-plane.

9. The axis cage of claim 5, wherein the surgical fasteners are adapted to interlock in a disc space above and below the one or more vertebrae or spinal column.

10. The axis cage of claim 5, wherein the surgical fasteners are adapted to penetrate different disc spaces between one or more vertebrae.

11. The axis cage of claim 5, wherein the interbody axis cage assembly is cannulated.

12. The axis cage of claim 5, wherein the segments are secured by one or more locking mechanisms.

13. The axis cage of claim 5, wherein the segments, frame, the rod, or the shaft comprises titanium, surgical alloys, stainless steel, chrome-molybdenum alloy, cobalt chromium alloy, zirconium oxide ceramic, non-absorbable polymers and other anticipated biocompatible metallic, ceramic or polymeric materials, and combinations thereof.

14. A method for stabilization, alignment, or support of one or more vertebrae comprising the steps of:
providing one or more vertebrae in need of stabilization, alignment, support or any combinations thereof and
implanting surgically an interbody axis cage assembly on one or more vertebrae, wherein the interbody axis cage assembly comprises
a flexible frame for attachment to a side of the one or more vertebrae, wherein the flexible frame comprises
a distal end comprising a first segment having a first body segment that separates a first vertical tab at a distal segment end and a first horizontal slot at a proximal end positioned perpendicular to the first vertical tab, and a first tab pin aperture positioned in the first vertical tab, and a first slot pin aperture positioned in the first horizontal slot, wherein the first tab pin aperture is positioned perpendicular to the first slot pin aperture;
a center section comprising a second segment having a second body segment that separates a second vertical tab at a distal segment end and a second horizontal slot at a proximal end positioned perpendicular to the second vertical tab, and a second tab pin aperture positioned in the second vertical tab, and a second slot pin aperture positioned in the second horizontal slot, wherein the second tab pin aperture is positioned perpendicular to the second slot pin aperture, wherein the second vertical tab mates to the first horizontal slot to align the first slot pin aperture and the second tab pin aperture to accept a first pivot pin;
a proximal end comprising a third segment having a third body segment that separates a third vertical tab at a distal segment end and a third horizontal slot at a proximal end positioned perpendicular to the third vertical tab and a third tab pin aperture positioned in the third vertical tab, and a third slot pin aperture positioned in the third horizontal slot, wherein the third tab pin aperture is positioned perpendicular to the third slot pin aperture, wherein the third vertical tab mates to the second horizontal slot to align the second slot pin aperture and the third tab pin aperture to accept a second pivot pin; and wherein the first segment pivots about the first pivot pin and the third segment pivots about the second pivot pin relative to the second segment such that the first segment pivots in a direction perpendicular to the pivot direction of the third segment; and
inserting one or more surgical fasteners at the distal end, the proximal end, and at one or more points along the center section to penetrate a disc space between the one or more vertebrae to attach the flexible frame to the side of the one or more vertebrae for stabilization, alignment, support, or any combinations thereof.

15. The method of claim 14, further comprising the step of using a flexible reamer or a cutter to aid in the placement of the interbody axis cage assembly.

16. The method of claim 14, further comprising the step of interlocking the surgical fasteners in the disc space or above or below the one or more vertebrae or spinal column.

17. The method of claim 14, further comprising the step of adjusting a X-plane and a Y-plane of the interbody axis cage.

18. The method of claim 14, wherein the interbody axis cage is cannulated.

19. The method of claim 14, further comprising the step of securing the distal end, the center section, and the proximal end with one or more locking mechanisms.

* * * * *